(12) United States Patent  (10) Patent No.: US 7,220,746 B2
Sterk  (45) Date of Patent: May 22, 2007

(54) PYRROLIDINEDIONE SUBSTITUTED PIPERIDINE-PHTHALAZONES AS PDE4 INHIBITORS

(75) Inventor: Geert Jan Sterk, Utrecht (NL)

(73) Assignee: Altana Pharma AG, Konstanz (DE)

( * ) Notice: Subject to any disclaimer, the term of this patent is extended or adjusted under 35 U.S.C. 154(b) by 0 days.

(21) Appl. No.: 10/523,412

(22) PCT Filed: Aug. 6, 2003

(86) PCT No.: PCT/EP03/08675

§ 371 (c)(1),
(2), (4) Date: Nov. 7, 2005

(87) PCT Pub. No.: WO2004/018457

PCT Pub. Date: Mar. 4, 2004

(65) Prior Publication Data

US 2006/0160813 A1    Jul. 20, 2006

(30) Foreign Application Priority Data

Aug. 10, 2002    (EP)    ................... 02017977

(51) Int. Cl.
*A61K 31/502* (2006.01)
*C07D 403/04* (2006.01)
*C07D 403/14* (2006.01)

(52) U.S. Cl. ..................... 514/248; 544/237

(58) Field of Classification Search ............... 514/248; 544/237

See application file for complete search history.

(56) References Cited

U.S. PATENT DOCUMENTS

| | | | |
|---|---|---|---|
| 5,376,656 | A | 12/1994 | Amschler |
| 5,716,954 | A | 2/1998 | Wilhelm et al. |
| 6,103,718 | A | 8/2000 | Sterk |
| 6,255,303 | B1 | 7/2001 | Sterk et al. |
| 6,380,196 | B1 | 4/2002 | Ulrich et al. |
| 6,544,993 | B1 | 4/2003 | Sterk |
| 6,756,371 | B1 | 6/2004 | Sterk |
| 2003/0195215 | A1 | 10/2003 | Sterk |
| 2004/0067946 | A1 | 4/2004 | Grundler et al. |
| 2004/0127707 | A1 | 7/2004 | Sterk |
| 2004/0132721 | A1 | 7/2004 | Grundler et al. |

FOREIGN PATENT DOCUMENTS

| | | |
|---|---|---|
| EP | 0 763 534 A1 | 3/1997 |
| WO | 92/06963 A1 | 4/1992 |
| WO | 93/07146 A1 | 4/1993 |
| WO | 94/12461 A1 | 6/1994 |
| WO | 98/31674 A1 | 7/1998 |
| WO | 99/31071 A1 | 6/1999 |
| WO | 99/31090 A1 | 6/1999 |
| WO | 99/47505 A1 | 9/1999 |
| WO | 01/19818 A1 | 3/2001 |
| WO | 01/30766 A1 | 5/2001 |
| WO | 01/30777 A1 | 5/2001 |
| WO | 01/94319 A1 | 12/2001 |
| WO | 02/064584 A1 | 8/2002 |
| WO | 02/085885 A1 | 10/2002 |
| WO | 02/085906 A2 | 10/2002 |
| WO | 02/085906 A3 | 10/2002 |

OTHER PUBLICATIONS

Vippagunta et al, "Crystalline Solids" Advanced Drug Delivery Reviews, vol. 48, pp. 3-26 (2001).*
Gavezzotti, "Are Crystal Structures Predictable?" Accounts of Chemical Research, vol. 27, pp. 309-314 (1994).*
Coates, W.J., et al., "1,4-Bis(3-oxo-2,3-dihydropyridazin-6-yl)benzene Analogues: Potent Phosphodiesterase Inhibitors and Inodilators", *J. Med. Chem.*, vol. 33, pp. 1735-1741, (1990).
Sotelo, E., et al., "Pyridazines. Part 25: Efficient and selective deprotection of pharmacologically useful 2-MOM-pyridazinones using Lewis acids", *Tetrahedron Letters*, vol. 42, pp. 8633-8636, (2001).
Van der May, M., et al., "Novel Selective PDE4 Inhibitors. 1. Synthesis, Structure-Activity Relationships, and Molecular Modeling of 4-(3,4-Dimethoxyphenyl)-2H-phthalazin-1-ones and Analogues", *J. Med. Chem.*, vol. 44, pp. 2511-2522, (2001).
Van der May, M., et al., "Novel Selective PDE4 Inhibitors. 2. Synthesis and Structure-Activity Relationships of 4-Aryl-Substituted cis-Tetra- and cis-Hexahydrophthalazinones", *J. Med. Chem.*, vol. 44, pp. 2523-2535, (2001).
Van der May, M., et al., "Novel Selective Phosphodiesterase (PDE4) Inhibitors. 4. Resolution, Absolute Configuration, and PDE4 Inhibitory Activity of cis-Tetra- and cis-Hexahydrophthalazinones", *J. Med. Chem.*, vol. 45, pp. 2526-2533, (2002).
Van der May, M., et al., "Novel Selective PDE4 Inhibitors. 3. In Vivo Antiinflammatory Activity of a New Series of N-Substituted cis-Tetra- and cis-Hexahydrophthalazinones", *J. Med. Chem.*, vol. 45, pp. 2520-2525, (2002).

* cited by examiner

*Primary Examiner*—Kahsay Habte
(74) *Attorney, Agent, or Firm*—The Nath Law Group; Joshua B. Goldberg; Sheldon M. McGee

(57) ABSTRACT

The compounds of formula I

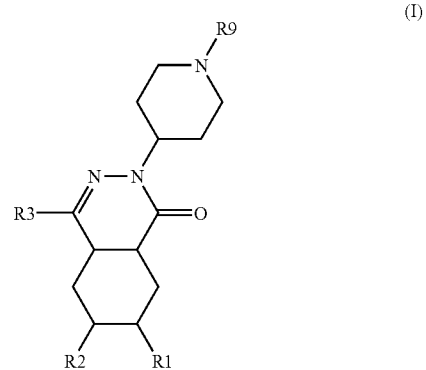

in which the substituents have the meanings as indicated in the description, are novel effective PDE4 inhibitors.

33 Claims, No Drawings

PYRROLIDINEDIONE SUBSTITUTED PIPERIDINE-PHTHALAZONES AS PDE4 INHIBITORS

FIELD OF APPLICATION OF THE INVENTION

The invention relates to novel piperidine-derivatives, which are used in the pharmaceutical industry for the production of pharmaceutical compositions.

KNOWN TECHNICAL BACKGROUND

International Patent Applications WO98/31674 (=U.S. Pat. No. 6,103,718), WO99/31071, WO99/31090, WO99/47505 (=U.S. Pat. No. 6,255,303), WO01/19818, WO01/30766, WO01/30777, WO01/94319, WO02/064584, WO02/085885 and WO02/085906 disclose phthalazinone derivatives having PDE4 inhibitory properties. In the International Patent Application WO94/12461 and in the European Patent Application EP 0 763 5343-aryl-pyridazin-6-one and arylalkyl-diazinone derivatives are described as selective PDE4 inhibitors. International Patent Application WO93/07146 (=U.S. Pat. No. 5,716,954) discloses benzo and pyrido pyridazinone and pyridazinthione compounds with PDE4 inhibiting activity.

In the Journal of Medicinal Chemistry, Vol. 33, No. 6, 1990, pp. 1735–1741 1,4-Bis(3-oxo-2,3-dihydropyridazin-6-yl)benzene derivatives are described as potent phosphodiesterase inhibitors and inodilators. In the Journal of Medicinal Chemistry Vol. 45 No.12, 2002, pp. 2520–2525, 2526–2533 and in Vol. 44, No. 16, 2001, pp. 2511–2522 and pp. 2523–2535 phthalazinone derivatives are described as selective PDE4 inhibitors.

DESCRIPTION OF THE INVENTION

It has now been found that the piperidine-derivatives, which are described in greater details below, have surprising and particularly advantageous properties.

The invention thus relates to compounds of formula 1 (1)

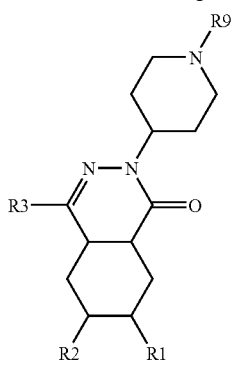

in which
R1 and R2 are both hydrogen or together form an additional bond,
R3 represents a phenyl derivative of formulae (a) or (b)

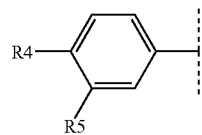

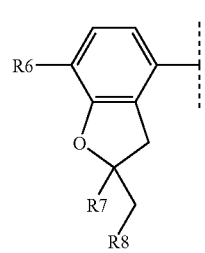

wherein
R4 is 1–4C-alkoxy or 1–4C-alkoxy which is completely or predominantly substituted by fluorine,
R5 is 1–4C-alkoxy, 3–7C-cycloalkoxy, 3–7C-cycloalkylmethoxy, or 1–4C-alkoxy which is or predominantly substituted by fluorine,
R6 is 1–4C-alkoxy or 1–4C-alkoxy which is completely or predominantly substituted by fluorine,
R7 is 1–4C-alkyl and
R8 is hydrogen or 1–4C-alkyl,
or wherein
R7 and R8 together and with inclusion of the two carbon atoms, to which they are bonded, form a spiro-linked 5-, 6- or 7-membered hydrocarbon ring, optionally interrupted by an oxygen or sulphur atom,
R9 is —C(O)—(CH$_2$)$_n$—R10,
wherein
R10 is pyrrolidine-2,5-dione-1-yl,
n is an integer from 1 to 4,
and the salts of these compounds.

If R1 and R2 together are an additional bond, then the carbon atoms in the positions 6 and 7 in the hexahydrophthalazinone ring system of the compounds of formula 1 are linked to one another via a double bond (→tetrahydrophthalazinone ring system).

1–4C-Alkyl is a straight-chain or branched alkyl radical having 1 to 4 carbon atoms. Examples are the butyl, isobutyl, sec-butyl, tert-butyl, propyl, isopropyl, ethyl and methyl radicals.

1–4C-Alkoxy is a radical which in addition to the oxygen atom, contains a straight-chain or branched alkyl radical having 1 to 4 carbon atoms. Alkoxy radicals having 1 to 4 carbon atoms which may be mentioned in this context are, for example, the butoxy, isobutoxy, sec-butoxy, tert-butoxy, propoxy, isopropoxy, ethoxy and methoxy radicals. Preferred are the methoxy and ethoxy radicals.

1–4C-Alkoxy which is completely or predominantly substituted by fluorine is, for example, the 2,2,3,3,3-pentafluoropropoxy, the perfluoroethoxy, the 1,2,2-trifluoroethoxy and in particular the 1,1,2,2-tetrafluoroethoxy, the 2,2,2-trifluoroethoxy, the trifluoromethoxy and the difluoromethoxy radical, of which the difluoromethoxy radical is preferred. "Predominantly" in this connection means that more than half of the hydrogen atoms of the 1–4C-alkoxy group are replaced by fluorine atoms.

3–7C-Cycloalkoxy stands for cyclopropyloxy, cyclobutyloxy, cyclopentyloxy, cyclohexyloxy or cycloheptyloxy, of which cyclopropyloxy, cyclobutyloxy and cyclopentyloxy are preferred.

3–7C-Cycloalkylmethoxy stands for cyclopropylmethoxy, cyclobutylmethoxy, cyclopentylmethoxy, cyclohexylmethoxy or cycloheptylmethoxy, of which cyclopropylmethoxy, cyclobutylmethoxy and cyclopentylmethoxy are preferred.

As spiro-linked 5-, 6- or 7-membered hydrocarbon rings, optionally interrupted by an oxygen or sulphur atom, may be mentioned the cyclopentane, cyclohexane, cycloheptane, tetrahydrofuran, tetrahydropyran and the tetrahydrothiophen ring.

Suitable salts for compounds of the formula 1 are all acid addition salts. Particular mention may be made of the pharmacologically tolerable inorganic and organic acids customarily used in pharmacy. Those suitable are water-soluble and water-insoluble acid addition salts with acids such as, for example, hydrochloric acid, hydrobromic acid, phosphoric acid, nitric acid, sulphuric acid, acetic acid, citric acid, D-gluconic acid, benzoic acid, 2-(4-hydroxybenzoyl) benzoic acid, butyric acid, sulphosalicylic acid, maleic acid, lauric acid, malic acid, fumaric acid, succinic acid, oxalic acid, tartaric acid, embonic acid, stearic acid, toluenesulphonic acid, methanesulphonic acid or 3-hydroxy-2-naphthoic acid, the acids being employed in salt preparation—depending on whether a mono- or polybasic acid is concerned and depending on which salt is desired—in an equimolar quantitative ratio or one differing therefrom.

Pharmacologically intolerable salts, which can be obtained, for example, as process products during the preparation of the compounds according to the invention on an industrial scale, are converted into pharmacologically tolerable salts by processes known to the person skilled in the art.

According to expert's knowledge the compounds of the invention as well as their salts may contain, e.g. when isolated in crystalline form, varying amounts of solvents. Included within the scope of the invention are therefore all solvates and in particular all hydrates of the compounds of formula 1 as well as all solvates and in particular all hydrates of the salts of the compounds of formula 1.

Compounds of formula 1 to be emphasized are those in which
R1 and R2 are both hydrogen or together form an additional bond,
R3 represents a phenyl derivative of formulae (a) or (b)

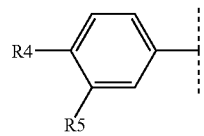

(a)

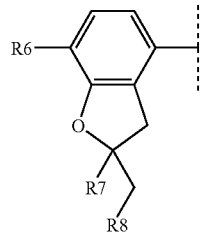

(b)

wherein
R4 is 1–2C-alkoxy or 1–2C-alkoxy which is completely or predominantly substituted by fluorine,
R5 is 1–2C-alkoxy or 1–2C-alkoxy which is completely or predominantly substituted by fluorine,
R6 is 1–2C-alkoxy or 1–2C-alkoxy which is completely or predominantly substituted by fluorine,
R7 is methyl and
R8 is hydrogen, or wherein
R7 and R8 together and with inclusion of the two carbon atoms, to which they are bonded, form a spiro-linked cyclopentane, cyclohexane, tetrahydrofurane or tetrahydropyran ring,
R9 is —C(O)—(CH$_2$)$_n$—R10,
wherein
R10 is pyrrolidine-2,5-dione-1-yl and
n is an integer from 1 to 2, and the salts of these compounds.

Compounds of formula 1 to be particularly emphasized are those, in which
R1 and R2 together form an additional bond,
R3 represents a phenyl derivative of formula (a)

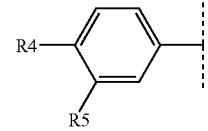

(a)

wherein
R4 is 1–2C-alkoxy,
R5 is 1–2C-alkoxy,
R9 is —C(O)—(CH$_2$)$_n$—R10,
wherein
R10 is pyrrolidine-2,5-dione-1-yl and
n is 1, and the salts of these compounds.

Preferred compounds of formula 1 are those in which
R1 and R2 together form an additional bond,
R3 represents a phenyl derivative of formula (a)

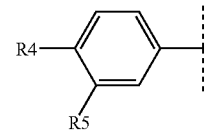

(a)

wherein
R4 is methoxy,
R5 is methoxy,
R9 is —C(O)—(CH$_2$)$_n$—R10,
wherein
R10 is pyrrolidine-2,5-dione-1-yl and
n is 1, and the salts of these compounds.

A special embodiment of the invention are those compounds of formula 1 in which R3 represents a phenyl derivative of formula (a).

Another special embodiment of the invention are those compounds of formula 1 in which R3 represents a phenyl derivative of formula (a) and n is 1.

Still another special embodiment of the invention are those compounds of formula 1 in which R1 and R2 form an additional bond and R3 represents a phenyl derivative of formula (a).

A further special embodiment of the invention are compounds of formula 1 in which R1 and R2 form an additional bond, R3 represents a phenyl derivative of formula (a) and n is 1.

Still a further special embodiment of the invention are compounds of formula 1 in which R1 and R2 form an additional bond, R3 represents a phenyl derivative of formula (b), R6 is methoxy, R7 is methyl, R8 is hydrogen, or R7 and R8 together and with inclusion of the two carbon atoms to which they are bonded form a spiro-linked cyclopentane or cyclohexane ring, and n is 1.

The compounds of formula 1 are chiral compounds. Chiral centers exist in the compounds of formula 1 in the positions 4a and 8a. In case R3 represents a phenyl derivative of formula (b) there is one further chiral center in the dihydrofuran-ring, if the substituents —R7 and —CH₂R8 are not identical. However, preferred are in this connection those compounds, in which the substituents —R7 and —CH₂R8 are identical or together and with inclusion of the two carbon atoms to which they are bonded form a spiro-connected 5-, 6- or 7-membered hydrocarbon ring.

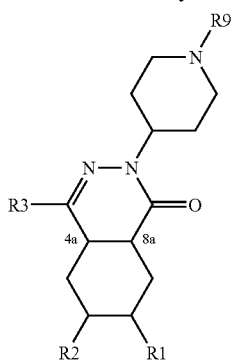
(1)

Numbering:

Therefore the invention includes all conceivable pure diastereomers and pure enantiomers of the compounds of formula 1, as well as all mixtures thereof independent from the ratio, including the race-mates. Preferred are those compounds of formula 1, in which the hydrogen atoms in the positions 4a and 8a are cis-configurated. Particularly preferred in this connection are those compounds, in which the absolute configuration (according to the rules of Cahn, Ingold and Prelog) is S in the position 4a and R in the position 8a.

Racemates can be split up into the corresponding enantiomers by methods known by a person skilled in the art. Preferably the racemic mixtures are separated into two diastereomers during the preparation with the help of an optical active separation agent on the stage of the cyclohexanecarboxylic acids or the 1,2,3,6-tetrahydrobenzoic acids (for example, starting compounds A8, A9 and A10).

As separation agents may be mentioned, for example, optical active amines such as the (+)- and (−)-forms of 1-phenylethylamine [(R)-(+)-1-phenylethylamine=(R)-(+)-α-methylbenzylamine or (S)-(−)-1-phenylethylamine=(S)-(−)-α-methylbenzylamine) and ephedrine, the optical active alkaloids quinine, cinchonine, cinchonidine and brucine.

The compounds according to the invention can be prepared, for example, as described In Reaction scheme 1.

Reaction scheme 1:

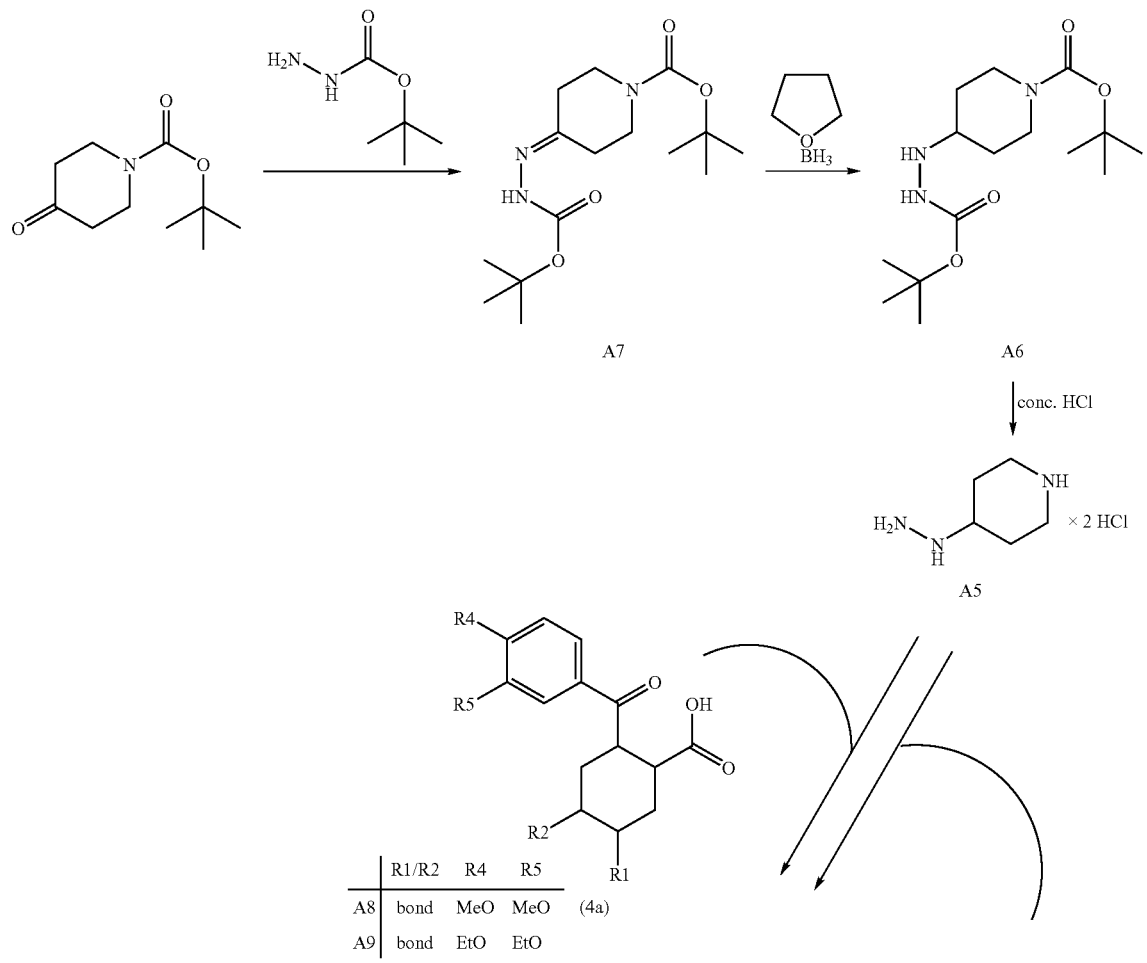

-continued

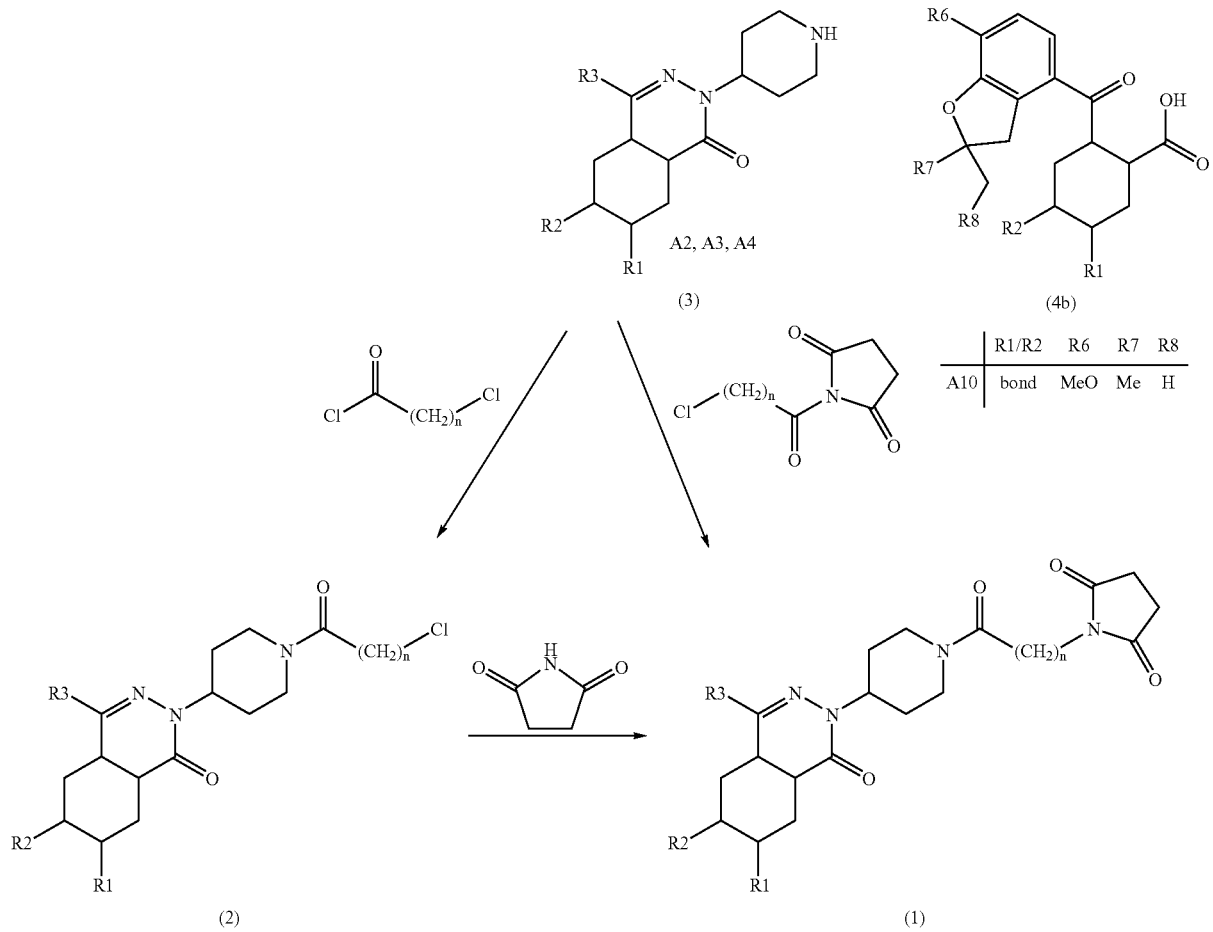

Reaction scheme 1 shows that the compounds of formula 1 can be, for example, prepared starting from 4-oxo-piperidine-1-carboxylic acid tert-butyl ester which is reacted in a first reaction step with tert-butylcarbazate to give 4-(tert-Butoxycarbonyl-hydrazono)-piperidine-1-carboxylic acid tert-butyl ester (starting compound A7). Compound A7 is reduced with, for example, the boran tetrahydrofurane complex to give 4-(N'-tert-Butoxycarbonyl-hydrazino)-piperidine-1-carboxylic acid tert-butyl ester (starting compound A6). Treatment of compound A6 with concentrated hydrochloric acid results in the formation of piperldin-4-yl-hydrazine dihydrochloride (starting compound A5).

The reaction of piperidin-4-yl-hydrazine dihydrochloride with benzoyl-1,2,3,6-tetrahydrobenzoic acids, benzoyl-1,2, 3,4,5,6hexahydrobenzoic acids, 2-[1-(2,3-dihydro-benzofuran-4-yl)methanoyl]-cyclohexane carboxylic acids or -cyclohexene carboxylic acids of formulae 4a or 4b leads to the piperidino derivatives of formula 3.

The piperidino derivatives of formula 3 are reacted with chloroacetyl chloride (3-chloropropionyl chloride, 4-chlorobutyryl chloride or 5-chloropentanoyl chloride) to give compounds of formula 2, which for their part are reacted in the final reaction step with pyrrolidine-2,5-dione to give the compounds of formula 1.

The reaction of the piperidino derivatives of formula 3 with chloroacetyl chloride (3-chloropropionyl chloride, 4-chlorobutyryl chloride or 5-chloropentanoyl chloride) is, for example, carried out in an inert solvent like acetone or homologues, acetonitrile, tetrahydrofurane, benzene, toluene, dioxane, (di-)ethyleneglycol ethers, dichloromethane, chloroform or homologues, ethyl acetate or pyridine, preferably in acetone, ethyl acetate or dichloromethane, in the presence of a suitable organic base, for example pyridine, quinoline, dimethylaniline, triethylamine or diisopropylethylamine, preferably triethylamine. Alternatively, the reaction is carried out in a two phase system of a solvent of the above mentioned list and water with one of the aforementioned organic bases or in a two phase system of a solvent of the abovementioned list and water containing an inorganic base such as sodium (or potassium) carbonate, sodium (or potassium) hydrogencarbonate or sodium (or potassium) hydroxide with or without an added quarternary alkylammonium phase transfer catalyst e.g. tetrabutylammonium chloride or a homologue thereof. In general, the reaction temperature is between −30 and +50° C., preferably the reaction temperature is about 0° C.

The reaction of the compounds of formula 2 with pyrrolidine-2,5-dione is carried out in a suitable inert solvent like acetone and homologues, acetonitrile, dimethylformamide, dimethylacetamide, N-methylpyrrolidone, dimethylsulfoxide, dioxane or diethylene glycol ethers, preferably dimethylformamide or butanone, in the presence of a suitable base, for example potassium, sodium, calcium or barium hydroxide or potassium or sodium carbonate; the preferred base is potassium carbonate. The reaction temperature can range from 0 to 150° C., preferred is a reaction temperature between 20 and 100° C.

In a variation of the above-mentioned reaction conditions a suitable basic salt of pyrrolidine-2,5-dione (for example, the potassium or sodium salt of pyrrolidine-2,5-dione) can be used directly instead of preparing it in situ by the addition of a suitable base to pyrrolidine-2,5-dione in the reaction mixture.

In an alternative synthesis route, the compounds of formula 3 can be reacted with 1-(2-chloroethanoyl)-pyrrolidine-2,5-dione [1-(3-chloro-propanoyl)-pyrrolidine-2,5-dione, 1-(4-chloro-butanoyl)-pyrrolidine-2,5-dione or 1-(5-chloro pentanoyl)-pyrrolidine-2,5-dione] to yield the compounds of formula 1.

The reaction of the compounds of formula 3 with 1-(2-chloro-ethanoyl)-pyrrolidine-2,5-dione [1-(3-chloro-propanoyl)-pyrrolidine-2,5-dione, 1-(4-chloro-butanoyl)-pyrrolidine-2,5-dione or 1-(5-chloro-pentanoyl)-pyrrolidine-2,5-dione] is carried out in a suitable inert solvent like acetone and homologues, acetonitrile, dimethylformamide, dimethylacetamide, N-methylpyrrolidone, dimethylsulfoxide, dioxane or diethylene glycol ethers, preferably dimethylformamide or butanone, in the presence of a suitable base, for example potassium, sodium, calcium or barium hydroxide or potassium or sodium carbonate; the preferred base is potassium carbonate. The reaction temperature can range from 0 to 150° C., preferred is a reaction temperature between 20 and 100° C.

The compounds of formula 1 prepared by the processes described above can then, if desired, be converted into their salts, or salts of the compounds of formula 1 obtained can then, if desired, be converted into the free compounds. Corresponding processes are known to the person skilled in the art.

The preparation of benzoyl-1,2,3,6-tetrahydrobenzoic acids, benzoyl-1,2,3,4,5,6-hexahydrobenzoic acids, 2-[1-(2,3-dihydro-benzofuran-4-yl)-methanoyl]-cyclohexane carboxylic acids or -cyclohexene carboxylic acids is known to the person skilled in the art (see for example Starting compounds and Intermediates).

1-(2-chloro-ethanoyl)-pyrrolidine-2,5-dione is commercially available. 1-(3-chloro-propanoyl)-pyrrolidine-2,5-dione, 1-(4-chloro-butanoyl)-pyrrolidine-2,5-dione or 1-(5-chloro-pentanoyl)-pyrrolidine-2,5-dione can be prepared according to processes known to the person skilled in the art; for example by reaction of the chloroalkanoyl chloride with the pyrrolidine-2,5-dione sodium, potassium or lithium salt in an inert solvent like for example tetrahydrofurane.

Suitably, the conversions are carried out analogous to methods which are familiar per se to the person skilled in the art, for example, in the manner which is described in the following examples.

The substances according to the invention are isolated and purified in a manner known per se, e.g. by distilling off the solvent in vacuo and recrystallising the residue obtained from a suitable solvent or subjecting it to one of the customary purification methods, such as column chromatography on a suitable support material.

Salts are obtained by dissolving the free compound in a suitable solvent (for example a ketone like acetone, methylethylketone, or methylisobutylketone, an ether, like diethyl ether, tetrahydrofuran or dioxane, a chlorinated hydrocarbon, such as methylene chloride or chloroform, or a low molecular weight aliphatic alcohol, such as ethanol, isopropanol) which contains the desired acid, or to which the desired acid is then added. The salts are obtained by filtering, reprecipitating, precipitating with a non-solvent for the addition salt or by evaporating the solvent. Salts obtained can be converted by basification into the free compounds which, in turn, can be converted into salts. In this manner, pharmacologically non-tolerable salts can be converted into pharmacologically tolerable salts.

The following examples illustrate the invention in greater detail, without restricting it. As well, further compounds of formula 1, of which the preparation is not explicitly described, can be prepared in an analogous way or in a way which is known by a person skilled in the art using customary preparation methods.

The compounds, which are mentioned in the examples as well as their salts are preferred compounds of the invention.

In the examples, RT stands for room temperature, h for hour(s), min for minute(s) and M. p. for melting point.

EXAMPLES

Final Products 1. 1-(2-{4-[(4aS,8aR)-4-(3,4-Dimethoxy-phenyl)-1-oxo-4a,5,8,8a-tetrahydro-yl]-piperidin-1-yl}-2-oxo-ethyl)-pyrrolidine-2,5-dione

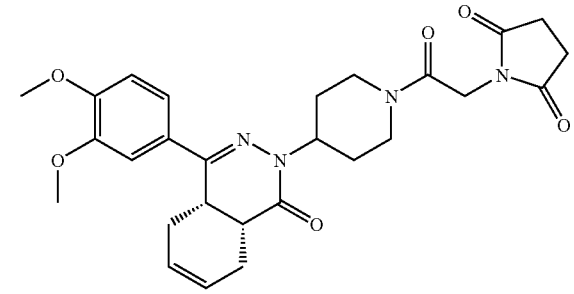

A mixture of 1 g of starting compound A1, 0.4 g of succinimide and 1 g of potassium carbonate in 20 ml of dimethylformamide is stirred for 18 h at RT, after which the mixture is diluted with 100 ml of ethyl acetate. After filtering this mixture, the solvent is evaporated and the residue purified by chromatography (ethyl acetate:methanol/2:1). The title compound is crystallized from ethyl acetate. M. p. 171–173° C.

Alternative Synthesis:

A mixture of 5 mmol of starting compound A2, 6 mmol of 1-(2-chloro-ethanoyl)-pyrrolidine-2,5-dione and 20 mmol of potassium carbonate in 20 ml of dimethylformamide is stirred at RT. After 18 h 100 ml of water and 300 ml of diethyl ether is added to the mixture. The ether solution is dried over magnesium sulfate. On concentrating the solution, the title compound crystallized. M. p. 171–173° C.

In a further alternative ethyl acetate is used instead of diethyl ether in the working up of the above mentioned alternative synthesis.

Starting Compounds and Intermediates

A1. (4aS,8aR)-2-[1-(2-Chloro-ethanoyl)-piperidin-4-yl]-4-(3,4-dimethoxy-phenyl)-4a,5,8,8a-tetrahydro-2H-phthalazine-1-one A solution of 10 g of chloroacetylchloride in 100 ml of dichloromethane is added slowly to a solution of 10 g of starting compound A2 and 20 ml of triethylamine in 100 ml of dichloromethane at 0° C. After complete addition, water is added to the reaction and the resulting mixture is stirred for 30 min. The dichloromethane layer is separated and washed with aqueous sodium carbonate. After drying and evaporating, the compound is purified by chromatography (ethyl acetate:petroleum ether (60-80° C.)/1:1) and crystallized from diethyl ether. M. p. 104–106° C.

A2. (4aS,8aR)-4-(3,4-Dimethoxy-phenyl)-2-piperidin-yl-4-a,5,8,8a-tetrahydro-2H-phthalazin-1-one hydrochloride A solution of 50 mmol of the salt of (S)-(−)-α-methylbenzylamine and (cis)-2-(3,4-dimethoxybenzoyl)-1,2,3,6-tetrahydrobenzoic acid (starting compound A8), 55 mmol of piperidin-4-yl-hydrazine dihydrochloride and 100 mmol of triethylamine in 150 ml of 1-propanol is refluxed for 18 h. After cooling to RT, the precipitate is filtered off and dried. M. p. 285–288° C.

A3. (4aS,8aR)-4-(3,4-Diethoxy-phenyl)-2-piperidin-4-yl-4a,5,8,8a-tetrahydro-2H-phthalazin-1-one hydrochloride Prepared from the salt of (S)-(−)-α-methylbenzylamine and (cis)-2-(3,4-diethoxybenzoyl)-1,2,3,6-tetrahydrobenzoic acid (starting compound A9) in 2-propanol as described for compound A2. M. p. 248–250° C.

A4. (cis)-4-(7-Methoxy-2,2-dimethyl-2,3-dihydro-benzofuran-4-yl)-2-piperidin-4-yl-4a,5,8,8a-tetrahydro-2H-phthalazine-1-one hydrochloride Prepared from (cis)-2-(2,3-Dihydro-2,2-dimethyl-7-methoxybenzofuran-4-carbonyl)-1,2,3,6-tetrahydrobenzoi acid (starting compound A10) in 1-propanol as described for compound A2. After evaporating the solvent, the residue is partitioned between dichloromethane and aqueous sodium carbonate. The dichlormethane layer is dried over magnesium sulfate and evaporated. The residue is dissolved in dichloromethane and after the addition of a solution of hydrochloric acid in ether, the compound precipitates. M. p. 288–290° C.

A5. Piperidin-4-yl-hydrazine dihydrochloride

A mixture of 0.1 mole of 4-(N'-tert-Butoxycarbonyl-hydrazino)-piperidine-1-carboxylic acid tert-butyl ester (starting compound A6) and 150 ml of concentrated hydrochloric acid is heated at 90° C. for 60 min after which the clear solution is evaporated. The residue is washed with tetrahydrofurane, filtered off and dried under vacuum. M. p. 256–259° C.

A6. 4-(N'-tert-Butoxycarbonyl-hydrazino)-piperidine-1-carboxylic acid tert-butyl ester 150 ml of a solution of borohydride in tertahydrofurane (1.0 mol/l) is slowly added to a solution of 0.12 mole of 4-(tert-Butoxycarbonyl-hydrazono)-piperidine-1-carboxylic acid tert-butyl ester (starting compound A7) in 100 ml of dry tetrahydrofurane. After complete addition, the mixture is stirred for another 30 min after which a 100 ml of water is added to destroy the excess of borohydride. Subsequently the tetrahydrofurane is evaporated and the resulting aqeous solution extracted with diethyl ether. After drying the solvent over magnesium sulfate, the ether is evaporated. M. p. 112–115° C.

A7. 4-(tert-Butoxycarbonyl-hydrazono)-piperidine-1-carboxylic acid tert-butyl ester A mixture of 0.15 mole of 4-oxo-piperidine-1-carboxylic acid tert-butyl ester (commercially available) and 0.15 mole of tert-butylcarbazate in 250 ml of hexane is stirred for 18 h at RT. The precipitate is filtered off and dried under vacuum. M. p. 172–174° C.

A8. (cis)-2-(3,4-Dimethoxybenzoyl)-1,2,3,6-tetrahydrobenzoic acid

Prepared as described in WO98/31674.

A9. (cis)-2-(3,4-diethoxybenzoyl)-1,2,3,6-tetrahydrobenzoic acid

Prepared as described in WO99/47505.

A10. (cis)-2-(2,3-Dihydro-2,2-dimethyl-7-methoxy-benzofuran-4-carbonyl)-1,2,3,6-tetrahydrobenzoic acid Prepared as described in WO99/31090.

Commercial Utility

The compounds according to the invention have useful pharmacological properties which make them industrially utilizable. As selective cyclic nucleotide phosphodiesterase (PDE) inhibitors (specifically of type 4), they are suitable on the one hand as bronchial therapeutics (for the treatment of airway obstructions on account of their dilating action but also on account of their respiratory rate- or respiratory drive-increasing action) and for the removal of erectile dysfunction on account of their vascular dilating action, but on the other hand especially for the treatment of disorders, in particular of an inflammatory nature, e.g. of the airways (asthma prophylaxis), of the skin, of the Intestine, of the eyes, of the CNS and of the joints, which are mediated by mediators such as histamine, PAF (platelet-activating factor), arachidonic acid derivatives such as leukotrienes and prostaglandins, cytokines, interleukins, chemokines, alpha-, beta- and gamma-interferon, tumor necrosis factor (TNF) or oxygen free radicals and proteases. In this context, the compounds according to the invention are distinguished by a good solubility, a good tolerability and a high potency in pharmacological in vivo models upon oral administration.

On account of their PDE-inhibiting properties, the compounds according to the invention can be employed in human and veterinary medicine as therapeutics, where they can be used, for example, for the treatment and prophylaxis of the following illnesses: acute and chronic (in particular inflammatory and allergen-induced) airway disorders of varying origin (bronchitis, allergic bronchitis, bronchial asthma, emphysema, COPD); dermatoses (especially of proliferative, inflammatory and allergic type) such as psoriasis (vulgaris), toxic and allergic contact eczema, atopic eczema, seborrhoeic eczema, Lichen simplex, sunburn, pruritus in the anogenital area, alopecia greata, hypertrophic scars, discoid lupus erythematosus, follicular and widespread pyodermias, endogenous and exogenous acne, acne rosacea and other proliferative, inflammatory and allergic skin disorders; disorders which are based on an excessive release of TNF and leukotrienes, for example disorders of the arthritis type (rheumatoid arthritis, rheumatoid spondylitis, osteoarthritis and other arthritic conditions), disorders of the immune system (AIDS, multiple sclerosis), graft versus host reaction, allograft rejections, types of shock (septic shock, endotoxin shock, gram-negative sepsis, toxic shock syndrome and ARDS (adult respiratory distress syndrome)) and also generalized inflammations In the gastrointestinal region (Crohn's disease and ulcerative colitis); disorders which are based on allergic and/or chronic, immunological false reactions in the region of the upper airways (pharynx, nose) and the adjacent regions (paranasal sinuses, eyes), such as allergic rhinitis/sinusitis, chronic rhinitis/sinusitis, allergic conjunctivitis and also nasal polyps; but also disorders of the heart which can be treated by PDE inhibitors, such as cardiac Insufficiency, or disorders which can be treated on account of the tissue-relaxant action of the PDE inhibitors, such as, for example, erectile dysfunction or colics of the kidneys and of the ureters in connection with kidney stones. In addition, the compounds of the invention are useful in the treatment of diabetes insipidus and conditions associated with cerebral metabolic inhibition, such as cerebral senility, senile dementia (Alz-heimer's disease), memory impairment associated with Parkinson's disease or multilnfarct dementia; and also illnesses of the central nervous system, such as depressions or arteriosclerotic dementia.

The Invention further relates to a method for the treatment of mammals, including humans, which are suffering from one of the above mentioned illnesses. The method is characterized in that a therapeutically active and pharmacologically effective and tolerable amount of one or more of the compounds according to the invention is administered to the ill mammal.

The invention further relates to the compounds according to the invention for use in the treatment and/or prophylaxis of illnesses, especially the illnesses mentioned.

The invention also relates to the use of the compounds according to the invention for the production of pharmaceutical compositions which are employed for the treatment and/or prophylaxis of the illnesses mentioned.

The invention furthermore relates to pharmaceutical compositions for the treatment and/or prophylaxis of the illnesses mentioned, which contain one or more of the compounds according to the invention.

Additionally, the invention relates to an article of manufacture, which comprises packaging material and a pharmaceutical agent contained within said packaging material, wherein the pharmaceutical agent is therapeutically effective for antagonizing the effects of the cyclic nucleotide phosphodiesterase of type 4 (PDE4), ameliorating the symptoms of an PDE4-mediated disorder, and wherein the packaging material comprises a label or package insert which indicates that the pharmaceutical agent is useful for preventing or treating PDE4-mediated disorders, and wherein said pharmaceutical agent comprises one or more compounds of formula 1 according to the invention. The packaging material, label and package insert otherwise parallel or resemble what is generally regarded as standard packaging material, labels and package inserts for pharmaceuticals having related utilities.

The pharmaceutical compositions are prepared by processes which are known per se and familiar to the person skilled in the art. As pharmaceutical compositions, the compounds according to the invention (=active compounds) are either employed as such, or preferably in combination with suitable pharmaceutical auxiliaries and/or excipients, e.g. in the form of tablets, coated tablets, capsules, caplets, suppositories, patches (e.g. as TTS), emulsions, suspensions, gels or solutions, the active compound content advantageously being between 0.1 and 95% and where, by the appropriate choice of the auxiliaries and/or excipients, a pharmaceutical administration form (e.g. a delayed release form or an enteric form) exactly suited to the active compound and/or to the desired onset of action can be achieved.

The person skilled in the art is familiar with auxiliaries or excipients which are suitable for the desired pharmaceutical formulations on account of his/her expert knowledge. In addition to solvents, gel formers, ointment bases and other active compound excipients, for example antioxidants, dispersants, emulsifiers, preservatives, solubilizers, colorants, complexing agents or permeation promoters, can be used.

The administration of the pharmaceutical compositions according to the Invention may be performed in any of the generally accepted modes of administration available in the art. Illustrative examples of suitable modes of administration include intravenous, oral, nasal, parenteral, topical, transdermal and rectal delivery. Oral delivery is preferred.

For the treatment of disorders of the respiratory tract, the compounds according to the invention are preferably also administered by inhalation in the form of an aerosol; the aerosol particles of solid, liquid or mixed composition preferably having a diameter of 0.5 to 10 µm, advantageously of 2 to 6 µm.

Aerosol generation can be carried out, for example, by pressure-driven jet atomizers or ultrasonic atomizers, but advantageously by propellant-driven metered aerosols or propellant-free administration of micronized active compounds from inhalation capsules.

Depending on the inhaler system used, in addition to the active compounds the administration forms additionally contain the required excipients, such as, for example, propellants (e.g. Frigen in the case of metered aerosols), surface-active substances, emulsifiers, stabilizers, preservatives, flavorings, fillers (e.g. lactose in the case of powder inhalers) or, if appropriate, further active compounds.

For the purposes of inhalation, a large number of apparatuses are available with which aerosols of optimum particle size can be generated and administered, using an inhalation technique which is as right as possible for the patient. In addition to the use of adaptors (spacers, expanders) and pear-shaped containers (e.g. Nebulator®, Volumatic®), and automatic devices emitting a puffer spray (Autohaler®), for metered aerosols, in particular In the case of powder inhalers, a number of technical solutions are available (e.g. Diskhaler®, Rotadisk®, Turbohaler® or the inhaler described in European Patent Application EP 0 505 321), using which an optimal administration of active compound can be achieved.

For the treatment of dermatoses, the compounds according to the invention are in particular administered in the form of those pharmaceutical compositions which are suitable for topical application. For the production of the pharmaceutical compositions, the compounds according to the invention (=active compounds) are preferably mixed with suitable pharmaceutical auxiliaries and further processed to give suitable pharmaceutical formulations. Suitable pharmaceutical formulations are, for example, powders, emulsions, suspensions, sprays, oils, ointments, fatty ointments, creams, pastes, gels or solutions.

The pharmaceutical compositions according to the invention are prepared by processes known per se. The dosage of the active compounds is carried out in the order of magnitude customary for PDE inhibitors. Topical application forms (such as ointments) for the treatment of dermatoses thus contain the active compounds in a concentration of, for example, 0.1–99%. The dose for administration by inhalation is customary between 0.1 and 3 mg per day. The customary dose in the case of systemic therapy (p.o. or i.v.) is between 0.03 and 3 mg/kg per day.

Biological Investigations

The second messenger cyclic AMP (cAMP) is well-known for inhibiting inflammatory and Immunocompetent cells. The PDE4 isoenzyme is broadly expressed in cells involved in the initiation and propagation of inflammatory diseases (H Tenor and C Schudt, in "Phosphodiesterase Inhibitors", 21–40, "The Handbook of Immunopharmacology", Academic Press, 1996), and its inhibition leads to an increase of the intracellular cAMP concentration and thus to the inhibition of cellular activation (JE Souness et al., Immunopharmacology 47: 127–162, 2000).

The antiinflammatory potential of PDE4 inhibitors in vivo in various animal models has been described (MM Teixeira, TiPS 18: 164–170, 1997). For the investigation of PDE4 inhibition on the cellular level (in vitro), a large variety of proinflammatory responses can be measured. Examples are the superoxide production of neutrophilic (C Schudt et al., Arch Pharmacol 344: 682–690, 1991) or eosinophilic (A Hatzelmann et al., Brit J Pharmacol 114: 821–831, 1995) granulocytes, which can be measured as luminol-enhanced chemiluminescence, or the synthesis of tumor necrosis factor-α in monocytes, macro-phages or dendritic cells (Gantner et al., Brit J Pharmacol 121: 221–231, 1997, and Pulmonary Pharmacol Therap 12: 377–386, 1999). In addition, the immunomodulatory potential of PDE4 inhibitors is evident from the inhibition of T-cell responses like cytokine synthesis or proliferation (DM Essayan, Biochem Pharmacol 57: 965–973, 1999). Substances which inhibit the secretion of the aforementioned proinflammatory mediators are those which inhibit PDE4. PDE4 inhibition by the compounds according to the invention is thus a central indicator for the suppression of inflammatory processes.

Method for Measuring Inhibition of PDE4 Activity

PDE4 activity was determined as described by Thompson et al. (Adv Cycl Nucl Res 10: 69–92, 1979) with some modifications (Bauer and Schwabe, Naunyn-Schmiedeberg's Arch Pharmacol 311: 193–198, 1980). At a final assay volume of 200 μl (96well microliter plates) the assay mixture contained 20 mM Tris (pH 7.4), 5 mM $MgCl_2$, 0.5 μM cAMP, [$^3$H]CAMP (about 30,000 cpm/assay), the test compound and an aliquot of cytosol from human neutrophils which mainly contains PDE4 activity as described by Schudt et al. (Naunyn-Schmiedeberg's Arch Pharmacol 344: 682–690, 1991); the PDE3-specific inhibitor Motapizone (1 μM) was included to suppress PDE3 activity originating from contaminating platelets. Serial dilutions of the compounds were prepared in DMSO and further diluted 1:100 (v/v) in the assays to obtain the desired final concentrations of the Inhibitors at a DMSO concentration of 1% (v/v) which by itself only slightly affected PDE4 activity.

After preincubation for 5 min at 37° C., the reaction was started by the addition of substrate (cAMP) and the assays were incubated for further 15 min at 37° C. 50 μl of 0.2 N HCl was added to stop the reaction and the assays were left on ice for about 10 min. Following incubation with 25 μg 5'-nucleotidase (Crotalus atrox snake venom) for 10 min at 37° C., the assays were loaded on QAE Sephadex A-25 (1 ml bed volume). The columns were eluted with 2 ml of 30 mM ammonium formiate (pH 6.0) and the eluate was counted for radioactivity. Results were corrected for blank values (measured in the presence of denatured protein) which were below 5% of total radioactivity. The amount of cyclic nucleotides hydrolyzed did not exceed 30% of the original substrate concentration. The $IC_{50}$-values for the compounds according to the invention for the inhibition of the PDE4 activity were determined from the concentration-inhibition curves by nonlinear-regression.

The inhibitory values determined for the compounds according to the invention follow from the following table A, in which the numbers of the compounds correspond to the numbers of the examples.

TABLE A

| Inhibition of PDE4 activity [measured as $-logIC_{50}$ (mol/l)] | |
|---|---|
| compound | $-logIC_{50}$ |
| 1 | 10.66 |

The invention claimed is:
1. A compound of formula I

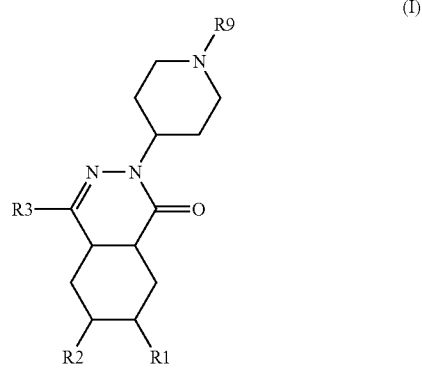

(I)

in which
R1 and R2 are both hydrogen or together form an additional bond,
R3 represents a phenyl derivative of formulae (a) or (b)

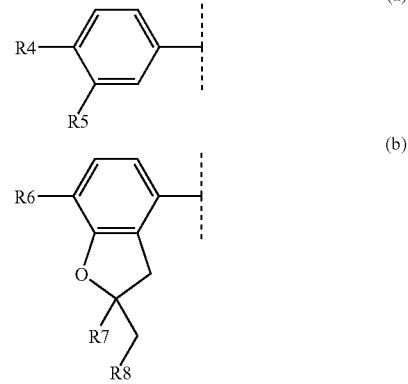

wherein
R4 is 1–4C-alkoxy or 1–4C-alkoxy which is completely or predominantly substituted by fluorine,
R5 is 1–4C-alkoxy, 3–7C-cycloalkoxy, 3–7C-cycloalkylmethoxy, or 1–4C-alkoxy which is completely or predominantly substituted by fluorine,
R6 is 1–4C-alkoxy or 1–4C-alkoxy which is completely or predominantly substituted by fluorine,
R7 is 1–4C-alkyl and
R8 is hydrogen or 1–4C-alkyl, or wherein R7 and R8 together, and with inclusion of the two carbon atoms to which they are bonded, form a spiro-linked 5-, 6- or 7-membered hydrocarbon ring, optionally interrupted by an oxygen or sulfur atom, R9 is —C(O)—(CH$_2$)$_n$-R10,
  wherein
  R10 is pyrrolidine-2,5-dione-1-yl,
  n is an integer from 1 to 4,
or a salt thereof.

2. A compound of formula I according to claim 1 in which
R1 and R2 are both hydrogen or together form an additional bond,
R3 represents a phenyl derivative of formulae (a) or (b)

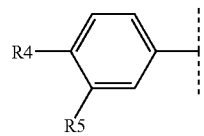

(a)

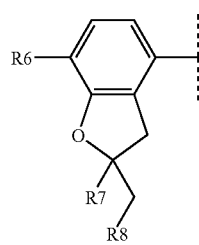

(b)

wherein
  R4 is 1–2C-alkoxy or 1–2C-alkoxy which is completely or predominantly substituted by fluorine,
  R5 is 1–2C-alkoxy or 1–2C-alkoxy which is completely or predominantly substituted by fluorine,
  R6 is 1–2C-alkoxy or 1–2C-alkoxy which is completely or predominantly substituted by fluorine,
  R7 is methyl and
  R8 is hydrogen,
  or wherein
  R7 and R8 together, and with inclusion of the two carbon atoms to which they are bonded, form a spiro-linked cyclopentane, cyclohexane, tetrahydrofurane or tetrahydropyran ring,
R9 is —C(O)—(CH$_2$)$_n$-R10,
  wherein
  R10 is pyrrolidine-2,5-dione-1-yl,
  n is an integer from 1 to 2, or a salt thereof.

3. A compound of formula I according to claim 1 in which
R1 and R2 together form an additional bond,
R3 represents a phenyl derivative of formula (a)

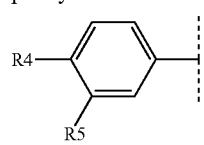

(a)

wherein
  R4 is 1–2C-alkoxy,
  R5 is 1–2C-alkoxy,
R9 is —C(O)—(CH$_2$)$_n$R10,
  wherein
  R10 is pyrrolidine-2,5-dione-1-yl and
  n is 1,
or a salt thereof.

4. A compound of formula I according to claim 1 in which
R1 and R2 together form an additional bond,
R3 represents a phenyl derivative of formula (a)

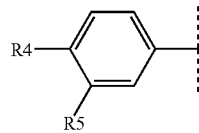

(a)

wherein
  R4 is methoxy,
  R5 is methoxy,
R9 is —C(O)—(CH$_2$)$_n$-R10,
  wherein
  R10 is pyrrolidine-2,5-dione-1-yl and
  n is 1,
or a salt thereof.

5. A compound of formula I according to claim 1, in which the hydrogen atoms in the positions 4a and 8a are cisconfigurated, or a salt thereof.

6. A compound of formula I according to claim 1, in which the absolute configuration is S in the position 4a and R in the position 8a, or a salt thereof.

7. A compound of formula I according to claim 1 with the chemical formula

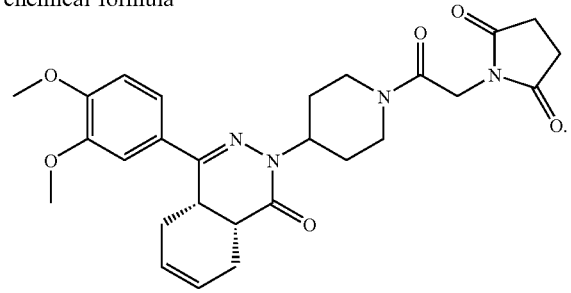

8. A compound of formula I according to claim 1 with the chemical formula

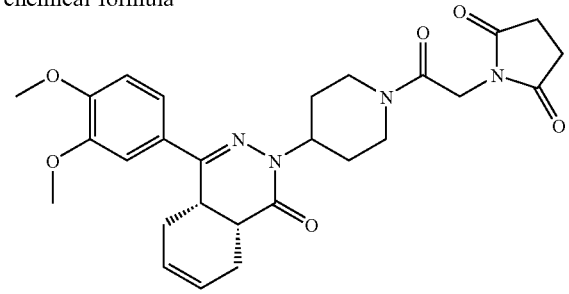

or a salt thereof.

9. A compound of formula I according to claim 1 with the chemical name 1-(2-{4-[(4aS,8aR)-4-(3,4-Dimethoxy-phenyl)-1-oxo-4a,5,8,8a-tetrahydro-1 H-phthalazin-2yl]-piperidin-1-yl}-2-oxo-ethyl)-pyrrolidine-2,5-dione.

10. A compound of formula I according to claim 1 with the chemical name 1-(2-{4-[(4aS,8aR)-4-(3,4-Dimethoxy-phenyl)-1-oxo-4a,5,8,8a-tetrahydro-1H-phthalazin-2-yl]-piperidin-1-yl}-2-oxo-ethyl)-pyrrolidine-2,5-dione or a salt thereof.

11. A process of preparing a compound comprising reacting (4aS,8aR)-4-(3,4-Dimethoxy-phenyl)-2-piperidin-4-yl-4a,5,8,8a-tetrahydro-2H-phthalazin-1-one hydrochloride with 1-(2chloro-ethanoyl)pyrrolidine-2,5-dione in the presence of a base.

12. A process of preparing 1-(2-{4[(4aS, 8aR)-4-(3,4-Dimethoxy-phenyl)-1-oxo-4a,5,8,8a-tetrahydro-1H-phthalazin-2yl]-piperidin-1-yl}-2oxo-ethyl)-pyrrolidine-2,5-dione comprising reacting (4aS, 8aR)-4-(3,4-Dimethoxyphenyl)-2-piperidin-4-yl-4a,5,8,8a-tetrahydro-2H-phthalazin-1-one hydrochloride with 1-(2-chloro-ethanoyl)-pyrrolidine-2,5-dione in the presence of a base.

13. A pharmaceutical composition comprising one or more compounds of formula I according to claim 1, or a pharmaceutically acceptable salt thereof, together with a suitable pharmaceutical auxiliary and/or excipient.

14. A method for treating airway disorders in a patient comprising administering to said patient a therapeutically effective amount of a compound of formula I as claimed in claim 1, or a pharmaceutically acceptable salt thereof.

15. A compound of formula I according to claim 2, in which the hydrogen atoms in the positions 4a and 8a are cis-configurated, or a salt thereof.

16. A compound of formula I according to claim 2, in which the absolute configuration is S in the position 4a and R in the position 8a, or a salt thereof.

17. A compound of formula I according to claim 3, in which the hydrogen atoms in the positions 4a and 8a are cisconfigurated, or a salt thereof.

18. A compound of formula I according to claim 3, in which the absolute configuration is S in the position 4a and R in the position 8a, or a salt thereof.

19. A compound of formula I according to claim 4, in which the hydrogen atoms in the positions 4a and 8a are cis-configurated, or a salt thereof.

20. A compound of formula I according to claim 4, in which the absolute configuration is S in the position 4a and R in the position 8a, or a salt thereof.

21. The method according to claim 14, wherein the airway disorder is selected from the group consisting of bronchitis, allergic bronchitis, bronchial asthma, emphysema, COPD and allergic rhinitis.

22. A method for treating dermatoses in a patient comprising administering to said patient a therapeutically effective amount of a compound of formula I as claimed in claim 1, or a pharmaceutically acceptable salt thereof.

23. The method according to claim 22, wherein the dermatose is selected from the group consisting of psoriasis and atopic eczema.

24. A pharmaceutical composition comprising the compound of claim 7 together with a suitable pharmaceutical auxiliary and/or excipient.

25. A pharmaceutical composition comprising the compound of claim 8, or a pharmaceutically acceptable salt thereof, together with a suitable pharmaceutical auxiliary and/or excipient.

26. A method for treating airway disorders in a patient comprising administering to said patient a therapeutically effective amount of the compound of claim 7.

27. A method for treating airway disorders in a patient comprising administering to said patient a therapeutically effective amount of the compound of claim 8 or a pharmaceutically acceptable salt thereof.

28. The method according to claim 26, wherein the airway disorder is selected from the group consisting of bronchitis, allergic bronchitis, bronchial asthma, emphysema, COPD and allergic rhinitis.

29. The method according to claim 27, wherein the airway disorder is selected from the group consisting of bronchitis, allergic bronchitis, bronchial asthma, emphysema, COPD and allergic rhinitis.

30. A method for treating dermatoses in a patient comprising administering to said patient a therapeutically effective amount of the compound of claim 7.

31. A method for treating dermatoses in a patient comprising administering to said patient a therapeutically effective amount of the compound of claim 8 or a pharmaceutically acceptable salt thereof.

32. The method according to claim 30, wherein the dermatose is selected from the group consisting of psoriasis and atopic eczema.

33. The method according to claim 31, wherein the dermatose is selected from the group consisting of psoriasis and atopic eczema.

* * * * *